United States Patent [19]

Shroot et al.

[11] Patent Number: 4,853,379
[45] Date of Patent: Aug. 1, 1989

[54] STABLE HYDROCORTISONE-BASED COMPOSITION FOR USE IN LOCAL CORTICOTHERAPY

[75] Inventors: Braham Shroot, Antibes; Carole Le Foyer de Costil; Liliane Ayache, both of Paris, all of France

[73] Assignee: Societe Anonyme dite: L'Oreal, Paris, France

[21] Appl. No.: 918,978

[22] Filed: Oct. 15, 1986

Related U.S. Application Data

[63] Continuation-in-part of Ser. No. 559,245, Dec. 8, 1983, abandoned.

[30] Foreign Application Priority Data

Dec. 9, 1982 [LU] Luxembourg ............................ 84515

[51] Int. Cl.$^4$ .............................................. A61K 31/56
[52] U.S. Cl. .................................... 514/179; 514/788; 514/859; 514/861; 514/863; 514/864; 514/975; 424/DIG. 13
[58] Field of Search ............... 514/179, 788, 859, 861, 514/863, 864, 975; 424/DIG. 13

[56] References Cited

U.S. PATENT DOCUMENTS

| 4,009,254 | 2/1977 | Renold | 424/59 |
| 4,243,548 | 1/1981 | Heeb et al. | 424/DIG. 1 |
| 4,305,936 | 12/1981 | Klein | 514/180 |
| 4,311,517 | 1/1982 | Youngman et al. | 514/643 |
| 4,323,558 | 4/1982 | Nelson | 424/164 |
| 4,353,896 | 10/1982 | Levy | 424/195.1 |

OTHER PUBLICATIONS

Baker, Physicians Desk Reference, 1982, p. 1899.
Windholz et al, eds, The Merck Index, 1976, pp. 629–630, "Hydrocortisone".
Osol et al, The Dispensatory of the United States of America, 1962, pp. 1134–1136.

*Primary Examiner*—Ronald W. Griffin
*Assistant Examiner*—Jacqueline M. Stone
*Attorney, Agent, or Firm*—Cushman, Darby & Cushman

[57] ABSTRACT

A stable hydrocortisone-based composition comprises hydrocortisone solubilized in a mixture of an aliphatic alcohol, propyleneglycol and dimethyl coco-benzylammonium chloride.

4 Claims, No Drawings

STABLE HYDROCORTISONE-BASED COMPOSITION FOR USE IN LOCAL CORTICOTHERAPY

This application is a continuation-in-part of application Ser. No. 559,245 filed Dec. 8, 1983 and now abandoned.

The present invention relates to a new composition for use in local corticotherapy, said composition capable of containing in the solubilized state, a high concentration of hydrocortisone, thereby avoiding undesirable side-effects which generally are encountered in a prolonged usage of hydrocortisone-based compositions.

Excessive and especially prolonged use of hydrocortisone-based lotions, ointments, creams or salves often is accompanied by certain secondary or side effects which cause, in the long run, a truly irreversible atrophy of the skin.

Known hydrocortisone-based compositions generally contain hydrocortisone in amounts lower than about 2 weight percent and more often in amounts of about 1 weight percent.

Compositions having a hydrocortisone concentration significantly less than this, i.e. in the order of 0.1 weight percent can be used principally to avoid the disadvantages attendant with the use of compositions having a higher hydrocortisone content. However, the duration of treatment is significantly longer and, consequently, the treatment requires medical supervision.

With the view of reducing the duration of the treatment and thus avoid undesirable side effects, hydrocortisone-based compositions in the form of dispersions have also been proposed. These compositions, even if they have a higher hydrocortisone content, nonetheless they also have been found to be less effective since they lack acceptable skin penetration characteristics on the areas of the skin to be treated.

Moreover, it has also been noted that these dispersion-type compositions exhibit poor storage stability characteristics, the hydrocortisone being degraded over a relatively short period of time which reduces to the same extent their activity.

Until now it has not been possible to perfect stable compositions for use in local corticotherapy which contain hydrocortisone in high concentrations and which exhibit good skin penetration characteristics and which in turn are capable of reducing the treatment time, thereby avoiding an irreversible atrophy of the skin.

This problem is resolved in accordance with the present invention by the use of a particular solvent mixture capable of solubilizing hydrocortisone in an amount greater than or equal to 2.5 weight percent based on the total weight of the composition.

Moreover, stability tests carried out on the compositions made in accordance with the present invention have shown excellent results, the rate of degradation, measured by HPLC, after a period of 2 months at ambient temperature, being lower than 5%.

The present invention thus relates to a stable hydrocortisone-based composition for use in local corticotherapy containing, in the solubilized state, hydrocortisone in a solvent mixture comprising an aliphatic alcohol having 1-3 carbon atoms, propyleneglycol, dimethyl coco-benzylammonium chloride, and water.

In accordance with the present invention, the aliphatic alcohol is methanol, ethanol or isopropanol, ethanol being more particularly preferred.

The dimethyl coco-benzylammonium chloride is a quaternary ammonium salt of the formula

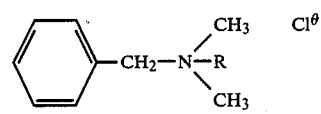

wherein
R represents the coco (or copra) radical which is a mixture of alkyl and alkenyl radicals having 6 to 18 carbon atoms, principally alkyl radicals having 12 to 14 carbon atoms.

In accordance with the present invention the solvent mixture comprises, preferably:
15 to 60 weight percent aliphatic alcohol having 1-3 carbon atoms,
15 to 60 weight percent propylene glycol,
3 to 30 weight percent of dimethyl coco-benzylammonium chloride, and
10 to 50 weight percent of water.

The solvent mixture is generally present in the composition of the present invention in an amount ranging from 40 to 99.99 weight percent based on the total weight of said composition.

The concentration of hydrocortisone in the compositions according to the present invention for use in local corticotherapy is generally not greater than 12 weight percent depending upon the solvent mixture employed. Preferably, however, the hydrocortisone is present in the compositions of the present invention in an amount between 0.01 and 5 weight percent, and more particularly between 0.5 and 4 weight percent, based on the total weight of the composition.

The compositions according to the present invention can be provided in various forms, principally in the form of lotions, shampoos, ointments or gels and are employed in the treatment of all ailments or diseases requiring local corticotherapy.

The lotions are essentially the hydrocortisone solubilized in said solvent mixture, to which optionally can be added conventional additives for this type of formulation.

The gels are obtained using gelling agents such as silica, cellulose derivatives, carboxyvinyl polymers (Carbopols), natural or synthetic gums, said gelling agent being employed in an amount varying between 0.5 and 15 percent by weight, relative to the total weight of the composition.

The ointments are anhydrous compositions based, for example, on petrolatum, paraffin oil or waxes.

The compositions according to the present invention are particularly useful in the treatment of eczema, psoriatic or eczematous erythrodermy, pruriginous lesions, chronic erythematous lupus, patch psoriasis and parapsoriasis, hyperthrophic cicatrix, and radiotherapic or solar erythema.

These treatments require an application of the composition of the present invention to the affected area of the skin, on the average, twice each day, optionally with a massaging action in order to facilitate the penetration thereof into the skin.

The following non-limiting examples are given to illustrate the compositions according to the present invention.

EXAMPLE A

Lotion for local corticotherapy
Propylene glycol: 30 g
Ethanol: 40 g
50% aqueous solution of dimethyl coco-benzylammonium chloride, sold under the tradename "Arquad DMMCB 50" by Akzo: 10 g
Hydrocortisone: 2.5 g
Water, sufficient amount for: 100 g

EXAMPLE B

Gel for local corticotherapy
Propylene glycol: 25 g
Ethanol: 40 g
50% aqueous solution of dimethyl coco-benzylammonium chloride: 10 g
Aerosil (finely divided silica) sold by Degussa: 8.5 g
Water: 14 g
Hydrocortisone: 2.5 g

EXAMPLE C

Shampoo for local corticotherapy
Propylene glycol: 20 g
Ethanol: 20 g
50% aqueous solution of dimethyl coco-benzylammonium chloride: 50 g
Hydrocortisone:
Water, sufficient amount for: 100 g Compositions A to C, above, are not only storage stable, but they also exhibit good skin penetration characteristics as well as good tolerance.

Relative to conditions usual in the use of hydrocortisone-based compositions, the treatment time when using the compositions of the present invention can be reduced in an appreciable manner, thus avoiding prolonged usage and undue risk of skin atrophy.

What is claimed is:

1. A hydrocortisone skin-penetrating composition for the treatment of eczema, psoriatic or eczematous erythrodermy, pruriginous lesions, chronic erythematous lupus, patch psoriasis and para-psoriasis, hyperthropic cicatrix and radiotherapic or solar erythema, said composition consisting essentially of 0.01 to 12 weight percent hydrocortisone based on the total weight of said composition, said hydrocortisone being solubilized in a hydrocortisone solubilizing mixture consisting essentially of (i) 15 to 60 weight percent based on the total weight of said mixture of an aliphatic alcohol selected from the group consisting of methanol, ethanol and isopropanol, (ii) 15 to 60 weight percent based on the total weight of said mixture of propylene glycol, (iii) 3 to 30 weight percent based on the total weight of said mixture of dimethyl coco benzyl ammonium chloride and (iv) 10 to 50 weight percent based on the total weight of said mixture of water.

2. The composition of claim 1 wherein said hydrocortisone is present in an amount ranging from 0.01 to 5 weight percent thereof.

3. The composition of claim 1 wherein said hydrocortisone is present in an amount ranging from 0.5 to 4 weight percent thereof.

4. The composition of claim 1 wherein said aliphatic alcohol is ethanol.

* * * * *